US012714584B2

(12) United States Patent
Malsbary et al.

(10) Patent No.: US 12,714,584 B2
(45) **Date of Patent: *Aug. 25, 2026**

(54) STENT GRAFT WITH BRACKETING STENT CONFIGURATIONS

(71) Applicant: Medtronic Vascular, Inc., Santa Rosa, CA (US)

(72) Inventors: Todd Malsbary, Santa Rosa, CA (US); Sydney Gustafson, Santa Rosa, CA (US); Justin Davison, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 841 days.

This patent is subject to a terminal disclaimer.

(21) Appl. No.: 17/965,314

(22) Filed: Oct. 13, 2022

(65) Prior Publication Data

US 2023/0031561 A1 Feb. 2, 2023

Related U.S. Application Data

(63) Continuation of application No. 17/066,035, filed on Oct. 8, 2020, now Pat. No. 11,517,456.

(51) Int. Cl.
*A61F 2/856* (2013.01)
*A61F 2/07* (2013.01)
(Continued)

(52) U.S. Cl.
CPC ................ *A61F 2/856* (2013.01); *A61F 2/07* (2013.01); *A61F 2/89* (2013.01);
(Continued)

(58) Field of Classification Search
CPC .......... A61F 2002/061; A61F 2002/065; A61F 2/07–2002/007; A61F 2002/828; A61F 2/856; A61F 2/89
See application file for complete search history.

(56) References Cited

U.S. PATENT DOCUMENTS 8,474,120 B2 7/2013 Hagaman et al.
9,662,196 B2 5/2017 Roeder et al.
(Continued)

FOREIGN PATENT DOCUMENTS

CN 103476359 B 7/2017
CN 106580518 B 11/2018
(Continued)

OTHER PUBLICATIONS

Japanese Office Action for Japanese Application No. 2021-163237, mailed May 29, 2025, 4 pages.
(Continued)

*Primary Examiner* — Leslie A Lopez
(74) *Attorney, Agent, or Firm* — Brooks Kushman P.C.

(57) ABSTRACT

The stent graft includes a main body and an external coupling. The main body extends along a longitudinal axis and includes proximal and distal ends. The external coupling extends away from the main body and defines an opening having a center. The main body includes a first bracketing stent extending about a proximal side of the external coupling. The first bracketing stent includes first and second peaks. The first peak is circumferentially aligned with the center of the external coupling. The first peak is proximal the second peak about the main body along the longitudinal axis.

20 Claims, 5 Drawing Sheets

(51) Int. Cl.
*A61F 2/89* (2013.01)
*A61F 2/06* (2013.01)
*A61F 2/82* (2013.01)

(52) U.S. Cl.
CPC ... *A61F 2002/061* (2013.01); *A61F 2002/065* (2013.01); *A61F 2002/828* (2013.01)

(56) References Cited

U.S. PATENT DOCUMENTS 9,839,542 B2 12/2017 Bruszewski et al.
10,485,684 B2 11/2019 Marmur et al.
2004/0215319 A1 10/2004 Berra et al.
2005/0102021 A1* 5/2005 Osborne .................. A61F 2/07 623/1.13
2010/0063576 A1* 3/2010 Schaeffer ................. A61F 2/07 623/1.13
2012/0271401 A1* 10/2012 Bruszewski ........... A61F 2/966 623/1.35
2013/0079870 A1* 3/2013 Roeder ..................... A61F 2/07 623/1.35
2014/0277335 A1 9/2014 Greenberg et al.
2017/0273809 A1* 9/2017 Marmur .................... A61F 2/07

FOREIGN PATENT DOCUMENTS

CN 109996514 A 7/2019
CN 109966016 B 2/2021
JP 2013071005 A 4/2013
JP 2014516633 A 7/2014
WO 2020100812 A1 5/2020

OTHER PUBLICATIONS

Extended European Search Report in European Application No. 21201208.2, mailed Sep. 26, 2022, 13 pages.
First Chinese Office Action for Chinese Application No. 202011278297, mailed May 6, 2026, 16 pages.

* cited by examiner

STENT GRAFT WITH BRACKETING STENT CONFIGURATIONS

CROSS-REFERENCE TO RELATED APPLICATION

This application is a continuation of U.S. application Ser. No. 17/066,035 filed Oct. 8, 2020, the disclosure of which is hereby incorporated in its entirety by reference herein.

TECHNICAL FIELD

The present disclosure relates to a stent graft with bracketing stent configurations.

BACKGROUND

The use of endovascular procedures has been established as a minimally invasive technique to deliver a variety of clinical treatments in a patient's vasculature. A stent graft is an implantable device made of a tube-shaped surgical graft covering and an expanding or self-expanding frame. The stent graft is placed inside a blood vessel to bridge, for example, an aneurismal, dissected, or other diseased or torn segment of the blood vessel, and, thereby, exclude the hemodynamic pressures of blood flow from the diseased segment of the blood vessel.

Depending on the region of the aorta involved, the aneurysm may extend into areas having vessel bifurcations or segments of the aorta from which smaller "branch" arteries extend. For example, thoracic aortic aneurysms can include aneurysms present in the ascending thoracic aorta, the aortic arch, and/or branch arteries that emanate therefrom, such as the left subclavian, left common carotid, or the brachiocephalic arteries. In some cases, a branched stent graft can be used to treat such aneurysms. For example, a branched stent graft can be deployed in the main vessel (e.g., aortic arch) with a coupling extending therefrom and toward or into the branched artery (e.g., left subclavian), and a supplemental, secondary stent graft can be deployed in the branched artery and connected to the coupling.

SUMMARY

In an embodiment, a stent graft includes a main body and an external coupling. The main body extends along a longitudinal axis and includes proximal and distal ends. The external coupling extends away from the main body and defines an opening having a center. The main body includes a first bracketing stent extending about a proximal side of the external coupling. The first bracketing stent includes first and second peaks. The first peak is circumferentially aligned with the center of the external coupling. The first peak is proximal the second peak about the main body along the longitudinal axis.

In an embodiment, a stent graft includes a main body and an external coupling. The main body extending along a longitudinal axis and including proximal and distal ends. The external coupling extends away from the main body. The main body includes a second bracketing stent extending about a distal side of the external coupling. The second bracketing stent includes a plurality of valleys aligned along a second axis. The first axis is oblique to the longitudinal axis. The second axis is perpendicular to the longitudinal axis.

In an embodiment, a stent graft includes a main body and an external coupling. The main body extends along a longitudinal and includes proximal and distal ends. The external coupling extends away from the main body. The main body includes an external coupling region including the external coupling and an opposite side region opposite the external coupling. The main body includes a first bracketing stent extending about a proximal side of the external coupling and a second bracketing stent extending about a distal side of the external coupling. The first bracketing stent includes a first plurality of peaks aligned along a first axis having first and second sections. The second bracketing stent includes a second plurality of peaks aligned along a second axis having third and fourth sections. The first and third sections are located in the external coupling region and diverge from each other. The second and fourth section are located in the opposite side region and converge toward each other.

DETAILED DESCRIPTION

Figure 1:
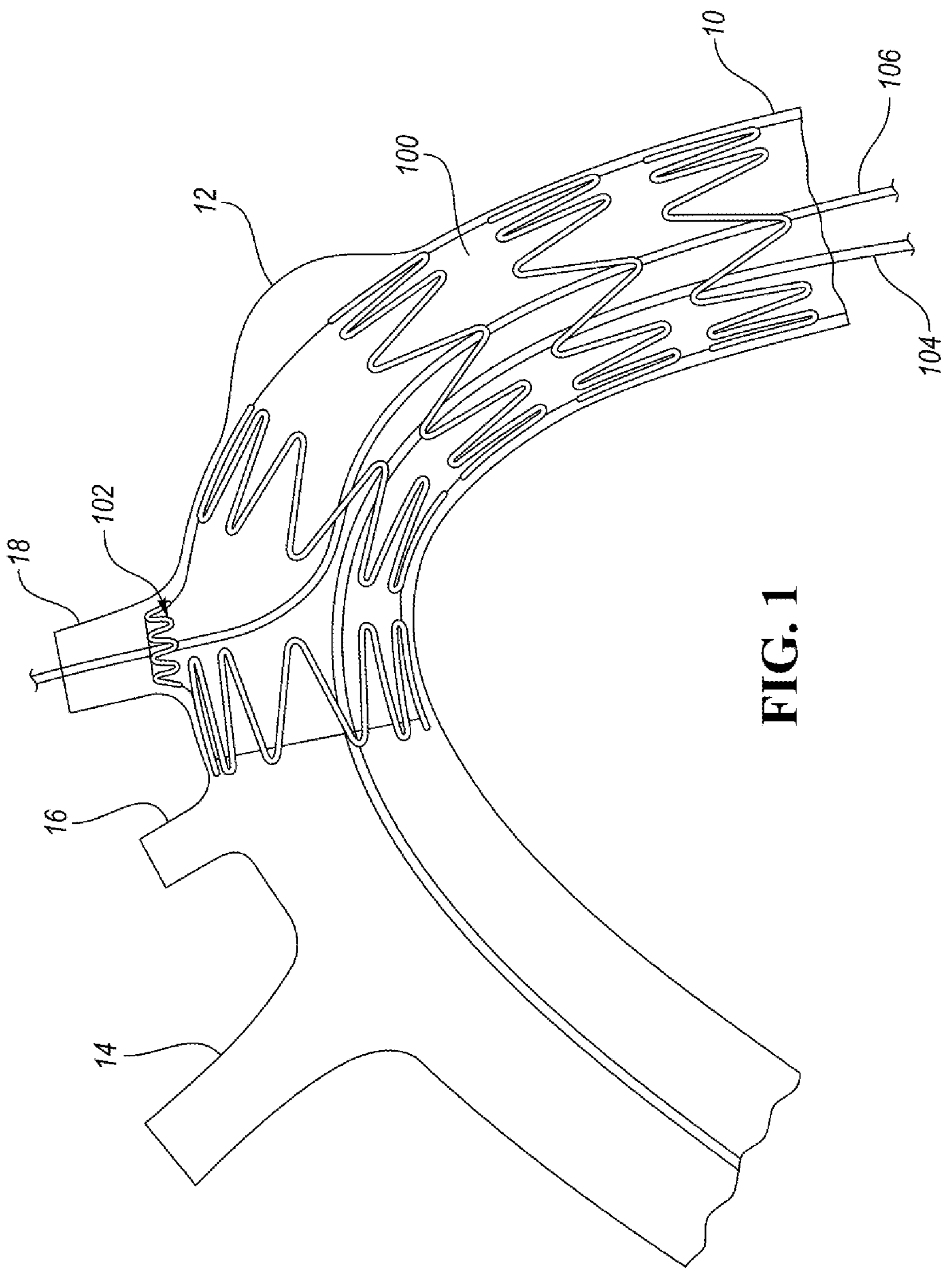
FIG. 1 is a schematic view of an aorta having a branched stent graft deployed therein, according to one embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis.

The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid and renal arteries, the invention may also be used in any other body passageways where it is deemed useful.

FIG. 1 illustrates a schematic of a blood vessel, in this case the aorta 10, with a branched stent graft 100 deployed therein. The branched stent graft 100 can be used for treatment of an aneurysm 12 of the aorta 10. The aorta 10 is shown with several branches, namely the brachiocephalic artery 14, the left common carotid artery 16, and the left subclavian artery 18. The branched stent graft 100 is "branched" in that it includes a branch extending into or toward one of the branches of the aorta 10. This branch of the stent graft can be referred to as a mobile external coupling, or more generally as a coupling 102. In this embodiment, the coupling 102 is positioned such that when the branched stent graft 100 is deployed, the coupling 102 is aligned with and extends into the left subclavian artery 18. Of course, in other embodiments the coupling 102 can be located on the branched stent graft 100 to align with and extend into the other branches of the aorta 10, such as the brachiocephalic artery 14 or the left common carotid artery 16. The placement of the coupling 102 in FIG. 1 is merely exemplary.

A primary guidewire 104 may first be inserted into the aorta 10. A secondary guidewire 106 may be inserted into the aorta 10, and into the desired branch where the coupling 102 is to be located, in this case the left subclavian artery 18. The primary guidewire 104 may be utilized for tracking the stent graft 100 along to the appropriate deployment site, and the secondary guidewire 106 may be utilized for tracking of a secondary stent graft (not shown) for deployment within the left subclavian artery 18. The stent grafts may be delivered using a stent graft delivery system, one embodiment of which is shown in FIG. 2 and described below.

During a surgical procedure, the stent graft delivery system may be utilized to track along both guidewires 104, 106, in which the delivery system includes lumens that each track along a respective one of the guidewires 104, 106. Deployment of the stent graft 100 may occur once situated in the proper location within the aorta 10. During deployment, the coupling 102 expands radially outwardly with the secondary guidewire extending through the coupling 102. Thereafter, the secondary stent graft (not shown) can track along the secondary guidewire 106, through the coupling 102, and into the left subclavian artery 18.

Figure 2:
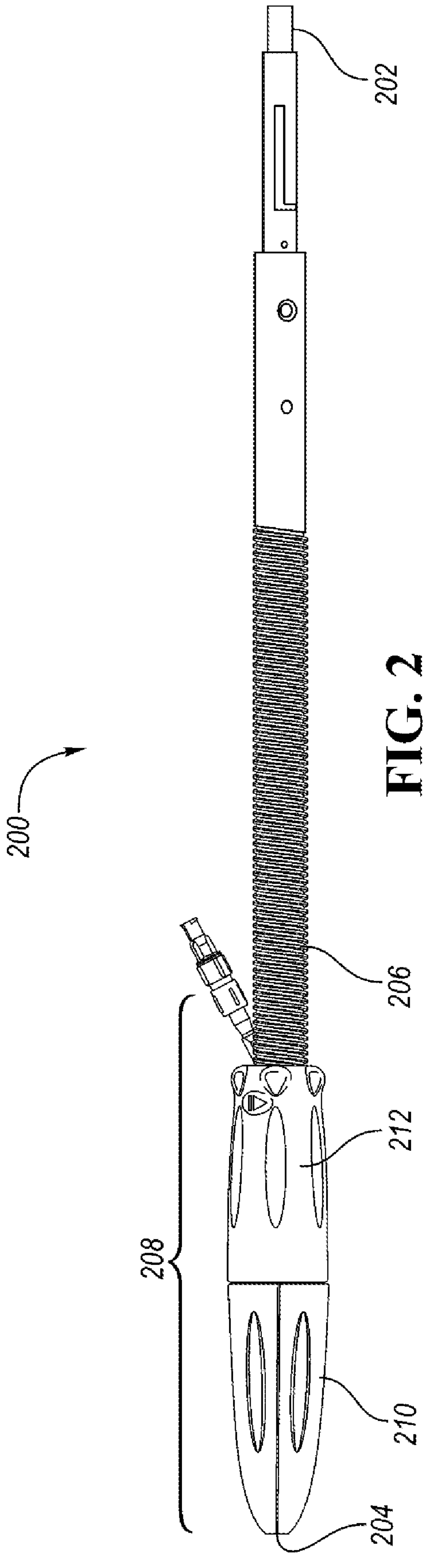
FIG. 2 is a side view of a delivery system for a branched stent graft, according to one embodiment.

FIG. 2 illustrates an example of such a branched stent graft delivery system 200 for delivering and deploying the branched stent graft 100 to the aorta 10. The delivery system 200 extends between a first end (e.g., proximal end) 202 and a second end (e.g., distal end) 204. A threaded screw gear 206 extends along an axis between the first end 202 and the second end 204. A handle assembly 208 is provided for grip by the clinician. The handle assembly 208 may include two separable portions, namely a front grip 210 and an external slider 212. The front grip 210 may be fixed relative to the screw gear 206, and the external slider 212 may rotate about a threaded outer surface of the screw gear 206 to move linearly along the screw gear 206. For example, during deployment of a stent graft (such as the branched stent graft 100), the external slider 212 is rotated to move toward the first end 202. The external slider 212 is operatively coupled to a stent graft cover (e.g., a sheath or lumen) surrounding the stent graft 100. This allows the sheath or lumen to be retracted with the linear movement of the external slider 212, thus allowing the stent graft 100 to radially expand within the aorta 10.

In a branched stent graft, such as the stent graft 100 of FIG. 1, the coupling should be flexible so that, during deployment of the stent graft, the coupling can easily move and shift into proper alignment with the desired artery. For example, the coupling can be flexible enough such that it can accommodate a relatively high degree (e.g., 30 degrees) of off-positioning of the stent graft in either the proximal, distal, anterior, or posterior directions. This flexibility is beneficial, as the terrain of the aorta 10 and its branched vessels can be tumultuous, and can vary amongst different patients. Such flexibility can also make the placement of the secondary stent graft a priority without compromising the position of the coupling or the location of the coupling along the stent graft.

Therefore, according to various embodiments described herein, a branched stent graft is provided with structure surrounding the coupling that is designed to improve the flexibility of the coupling without sacrificing its structural makeup.

FIGS. 3A-5B illustrate various views of a branched stent graft 300, according to an embodiment. The stent graft 300 is shown in a radially-expanded configuration, not installed into a blood vessel of a patient. In other words, the stent graft 300 is shown in these Figures in a preinstalled configuration in which the stent graft 300 is not yet compacted or compressed to fit within a catheter for insertion into a body of a patient.

Figures 3A, 3B:
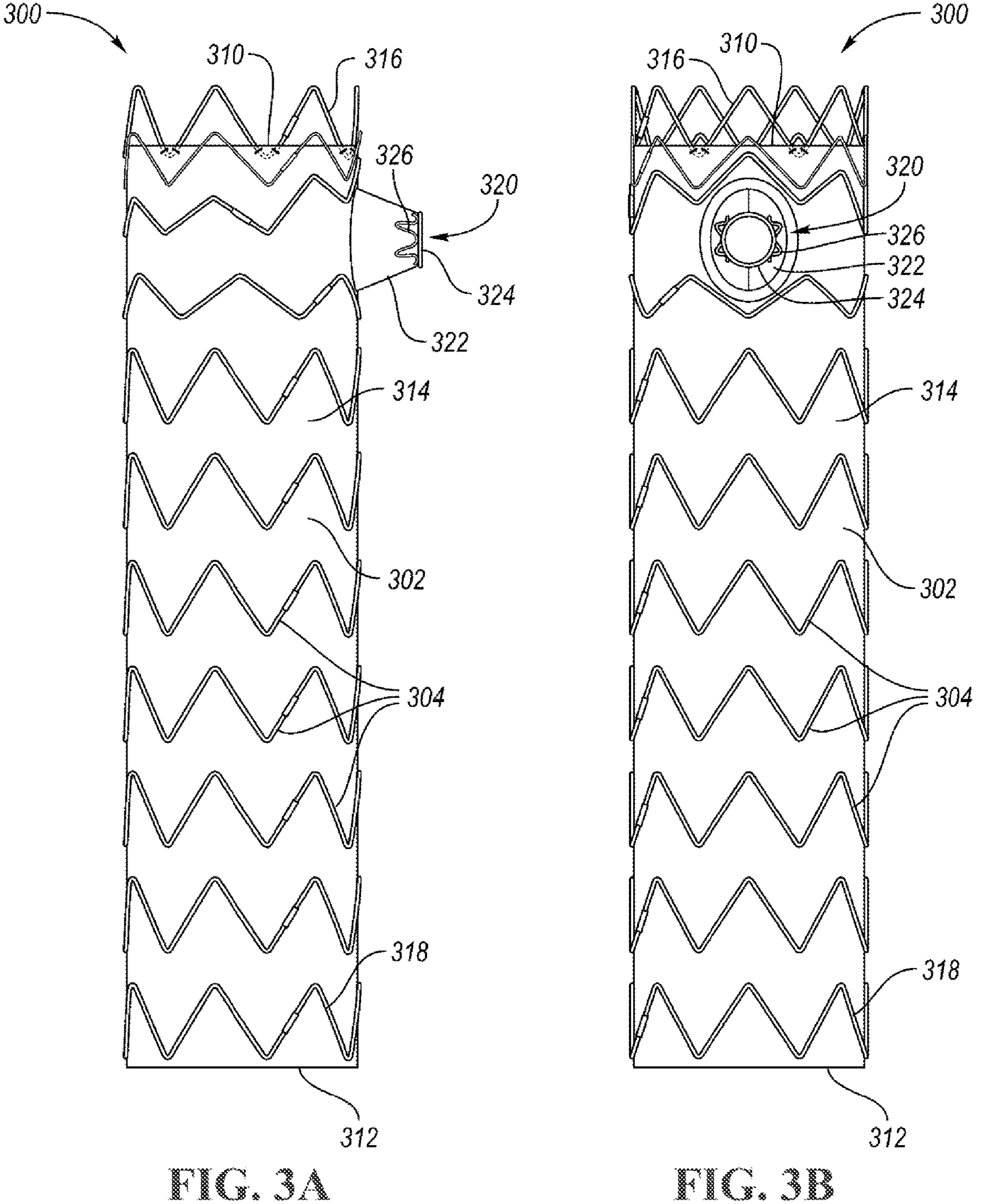
FIG. 3A is a side view of a branched stent graft according to one embodiment.
FIG. 3B is another side view of the branched stent graft of FIG. 3A, rotated 90 degrees relative to the view of FIG. 3A.

FIGS. 3A and 3B illustrate a branched stent graft 300, according to one embodiment. The branched stent graft, also referred to as a main stent graft or simply a stent graft, can be configured for treatment of the aorta 10 and its branched arteries, as described above. The branched stent graft 300 can also be delivered and deployed using a stent graft delivery system, such as the delivery system 200 of FIG. 2.

The branched stent graft 300 can be self-expanding, in that it includes structures that are shaped or formed form a material that can be provided with a mechanical memory to return the structure from a compressed or constricted delivery configuration to an expanded deployed configuration. In this embodiment, the stent graft includes a tubular graft 302 (also referred to as a body), and one or more stents 304 for supporting and expanding the graft 302.

The graft 302 may be formed from any blood-impermeable material graft material, for example a low-porosity woven or knit polyester, DACRON material, expanded polytetrafluoroethylene, polyurethane, silicone, or the like. In another embodiment, the graft material is a natural material such as pericardium or another membranous tissue such as intestinal submucosa.

The stents 304 are radially-compressible and expandable, and are coupled (e.g., via stitching or suturing, laminated between layers of fabric, etc.) to the material of the graft 302 for supporting the graft 302. The stents 304 are operable to self-expand into apposition with the interior wall of the aorta 10. Each stent 304 may be constructed from a self-expanding or spring material, such as but not limited to nickel-titanium alloy (Nitinol), stainless steel, a pseudo-elastic metal such as a nickel titanium alloy or nitinol, various polymers, or a so-called super alloy, which may have a base metal of nickel, cobalt, chromium, or other metal, or other suitable material. The stents 304 may be fixed in a sinusoidal (or zig zag) patterned ring about the circumference of the graft 302.

The stent graft 300 includes a proximal end 310, a distal end 312, and a main body 314 therebetween. The proximal end 310 may be provided with a proximal stent 316, also referred to as a bare stent, anchor stent, or crown stent. The proximal stent 316 may extend outside of the graft material 302 such that it is configured to anchor to the inner walls of the vessel (e.g., aorta) 10. In this embodiment, a majority of the proximal stent 316 extends proximally beyond the graft material 302 such that a majority of the proximal stent 316 is not directly connected to the graft material 302. Likewise, the distal end 312 may be provided with a distal stent 318. In the illustrated embodiment, the distal stent 318 does not extend distally beyond the graft material 302; however, in other embodiments, the distal stent 318 can be at least partially exposed, extending distally beyond the graft material 302 at the distal end 312 such that it too can be configured to anchor to the vessel.

The stent graft 300 also includes a mobile external coupling 320 (or, coupling) which can be designed and constructed similar to the coupling 102 described above. The coupling 320 is disposed on an outer surface of the stent graft 300 at a location corresponding to an opening in the graft material. The mobile external coupling 320 is generally frustoconical-shaped, or volcano-shaped with sloped side walls 322 leading to an open top or opening 324. The mobile external coupling 320 may be made of graft material that corresponds or matches to the graft material 302 of the body 314, although the graft material of the coupling 320 can be a separate piece of graft material (e.g., different material composition, thickness, etc.) attached to the graft material 302. A circumferential stent or annular stent 326 may be coupled to the graft material of the coupling 320 around the open top 324 of the mobile external coupling 320. Also, the stent 326 may be formed of similar material as the other stents 304 of the stent graft 300. As shown, the stent 326 may have a zig-zag or sinusoidal configuration around the top 324 of the mobile external coupling 320. Additional description of the mobile external coupling 120 may be found in U.S. Pat. No. 9,839,542, which is hereby incorporated by reference in its entirety. U.S. Pat. No. 9,839,542 also includes examples of dual guidewire delivery systems. Aspects of the devices, delivery systems, and/or deployment methods of U.S. Pat. No. 9,839,542 may be combined with those of the present disclosure.

Figures 4A, 4B:
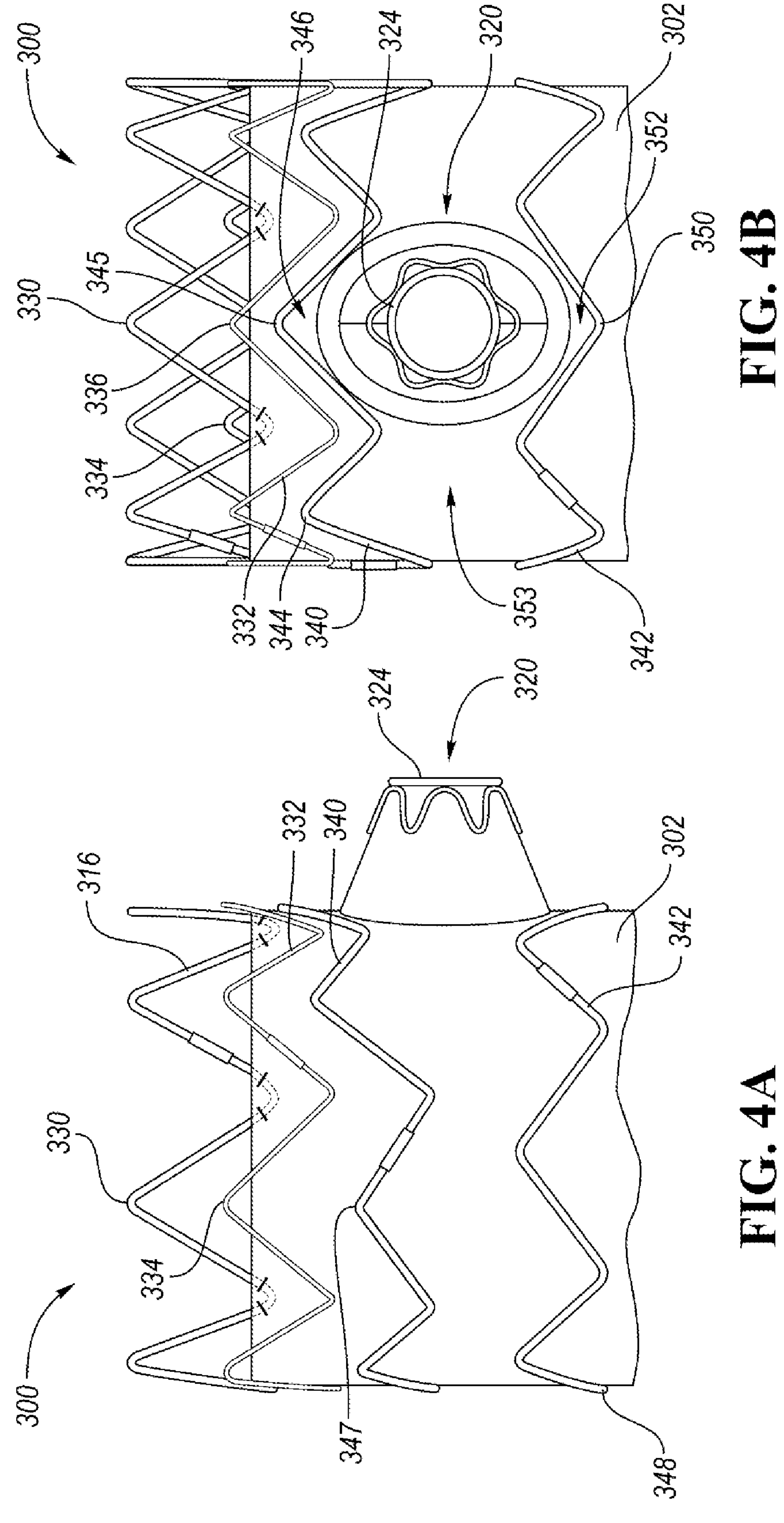
FIG. 4A is an enlarged side view of a portion of the stent graft of FIG. 3A, according to one embodiment.
FIG. 4B is another enlarged side view of the branched stent graft of FIG. 3A, rotated 90 degrees relative to the view of FIG. 4A.

FIGS. 4A-4B are enlarged views of FIGS. 3A-3B, focusing on the region near the proximal end 310 and mobile external coupling 320. The proximal stent 316 has peaks 330 that are bare, extending beyond the proximal end of the graft material 302. In this embodiment, the proximal stent 316 has seven peaks 330, and they extend generally uniform about the central longitudinal axis of the stent graft 300. Thus, in FIG. 4A, some peaks 330 to the rear of the stent graft 300 are overlapped by the peaks 330 to the front of the stent graft 300 when looking from the orientation shown in FIG. 4A. With an odd number of peaks 330 and the spacing of the peaks 330 being generally uniform, the proximal stent 316 aligns or overlaps itself when looking from a certain angular orientation about the central axis, such as the view shown in FIG. 4A.

The proximal stent 316 can be stitched, sutured, or otherwise attached to the inside surface of the graft material 302, as is shown in FIGS. 4A-4B. While the proximal stent 316 is shown attached to the inside of the graft material 302 in this embodiment, it may alternatively be attached to the outside of the graft material.

The stent graft 300 also includes a support stent 332. The support stent 332 is directly adjacent the proximal stent 316 with no intervening stents therebetween. The support stent 332 is configured to provide additional support for the stent graft 302 in the region between the mobile external coupling 320 and the proximal end 310. As the coupling 320 bends and flexes during placement within the treated vessel, the support stent 332 allows the coupling 320 to maintain flexibility without sacrificing the structural integrity of the main body 314 of the stent graft 300. In other words, the support stent 332 can facilitate the relative flexing of the coupling 320 relative to the main body 314. The support stent 332 may also improve the seal of the proximal end 310 with the vessel wall.

This function of the support stent 332 can be provided in multiple ways. In one or more embodiment, the support stent 332 is thinner than the proximal stent 316 and/or the other remaining stents of the stent graft 300. For example, while the thickness of the stents 304, 316 may be 0.50 millimeters (mm) thin, the support stent 332 may be 0.25 mm thin. This can provide the proper balance of allowing flexibility while maintaining structural integrity. Furthermore, in one or more embodiment, the support stent 332 has various peaks 334 that extend beyond the proximal end of the graft material 302. These peaks 334 are exposed, similar to the peaks 330 of the proximal stent 316. However, unlike the proximal stent 316, a majority (e.g., 75 percent) of the support stent 332 is directly attached to or overlaps with the graft material 302 (i.e., a majority of the support stent 332 does not extend proximally beyond the graft material 302). This allows the peaks 334 to allow the stents to make additional contact (e.g., two points of contact) with the treated vessel; both the proximal stent 316 and the support stent 332 are configured to contact the treated vessel upon deployment of the stent graft 300, in locations where the graft material 302 is not present. Also, a minority (greater than zero, such as within a range of 1 to 25 percent) of the support stent 332 is located proximal of the proximal end (e.g., not directly attached to or overlapping with the graft material 302).

Moreover, the peaks 334 can be circumferentially aligned with the peaks 330, such that each peak 334 is circumferentially aligned with a corresponding one of the peaks 330, as shown in FIGS. 4A-4B. In other words, the support stent 332 can be referred to as being aligned "in phase," with the proximal stent 316, such that the peaks and valleys of the stents 316, 332 follow the same general circumferential pattern. The support stent 332 may have the same number of peaks as the proximal stent (e.g., seven in the embodiment shown). While the proximal stent 316 is attached to the inside surface of the graft material 302, the support stent 332 may be attached (e.g., stitched, sutured, etc.) to the outside surface of the graft material 302. However, in other embodiments, the proximal and supports stents may be attached on the opposite surfaces or on the same surface (inner or outer).

The support stent 332 (and therefore the proximal stent 316) may be circumferentially oriented such that one of the peaks 336 is circumferentially aligned with the opening 324 of the coupling 320 (e.g., the center of the opening). This provides additional room for a bracketing stent 340 (described below) to be disposed axially between the coupling 320 and the proximal end 310/support stent 332. Also, by aligning the peak 336 with the opening 324, this allows maximum flex and deflection of the coupling 320 in the axial direction of the main body 314 without interference from the support stent 332.

The stent graft 300 also includes a pair of bracketing stents, namely a first bracketing stent 340 and a second bracketing stent 342. The first and second bracketing stents 340, 342 are each axially adjacent to the coupling 320, in that no other stents are provided between the stents 340, 342 and the coupling 320. The first bracketing stent 340 is located proximally adjacent the coupling 320, and the second bracketing stent 342 is located distally adjacent the coupling 320. The first bracketing stent 340 may provide a "hi-lo" design, with the first bracketing stent 340 having a peak 345 circumferentially aligned with a center of the opening 324, and "higher" than another peak 347 of the stent 340. This "hi-lo" design can also apply for the second bracketing stent 342.

In one or more embodiments, the first bracketing stent 340 is circumferentially in phase with the proximal stent 316 and the support stent 332; peaks 344 of the first bracketing stent 340 are circumferentially aligned with peaks 334 of the support stent 332, and peaks 330 of the proximal stent 316. The first bracketing stent 340 may have the same number of peaks as the support stent 332 and proximal stent 316. Thus, one of the peaks 344 (i.e., peak 345) is circumferentially aligned with a center of the opening 324 of the coupling 320, thus providing the coupling with flexibility without sacrificing structural integrity of the main body of the stent graft 300. This also provides an open area 346 of graft material 302 without a stent immediately proximally adjacent the coupling 320, which provides additional flexibility for alignment of the coupling 320 within the treated vessel. If there is misalignment of the coupling 320 during installation, there will not be a stent pushing on the proximal side of the coupling 320 that could otherwise cause an unwanted bending of the coupling 320 during realignment of the stent graft 300.

In one or more embodiments, the second bracketing stent 342 has a different number of peaks (e.g., one less peak) than the first bracketing stent 340, support stent 332, and proximal stent 316. In one embodiment, stents 316, 332, and 340 have seven peaks and the second bracketing stent 342 has six peaks. Thus, the second bracketing stent 342 is not in phase with the first bracketing stent 340, support stent 332, or proximal stent 316 all the way circumferentially about the stent graft 300. In the illustrated embodiment, the second bracketing stent has a valley 348 (e.g., a part of the stent that is located most distally) that is in phase and in circumferential alignment with corresponding valleys of the first bracketing stent 340, support stent 332, and proximal stent 316. This valley 348 is located on an opposite side of the stent graft 300 from the coupling 320 (e.g., the side configured to contact an inner curve of the aortic arch). Moreover, as shown in FIG. 4B, the second bracketing stent 342 becomes 180-degrees out of phase with those stents 340, 332, 316 at a location circumferentially aligned with the opening 324 of the coupling 320. In other words, the second bracketing stent 342 has a valley 350 that is circumferentially aligned with the peaks 330, 336, 344 and the opening 324. The valley 350 is circumferentially opposite from the valley 348. This provides an open area 352 of graft material 302 without a stent immediately distally adjacent the coupling 320, which provides similar function and benefits as the opening 346.

Figures 5A, 5B:
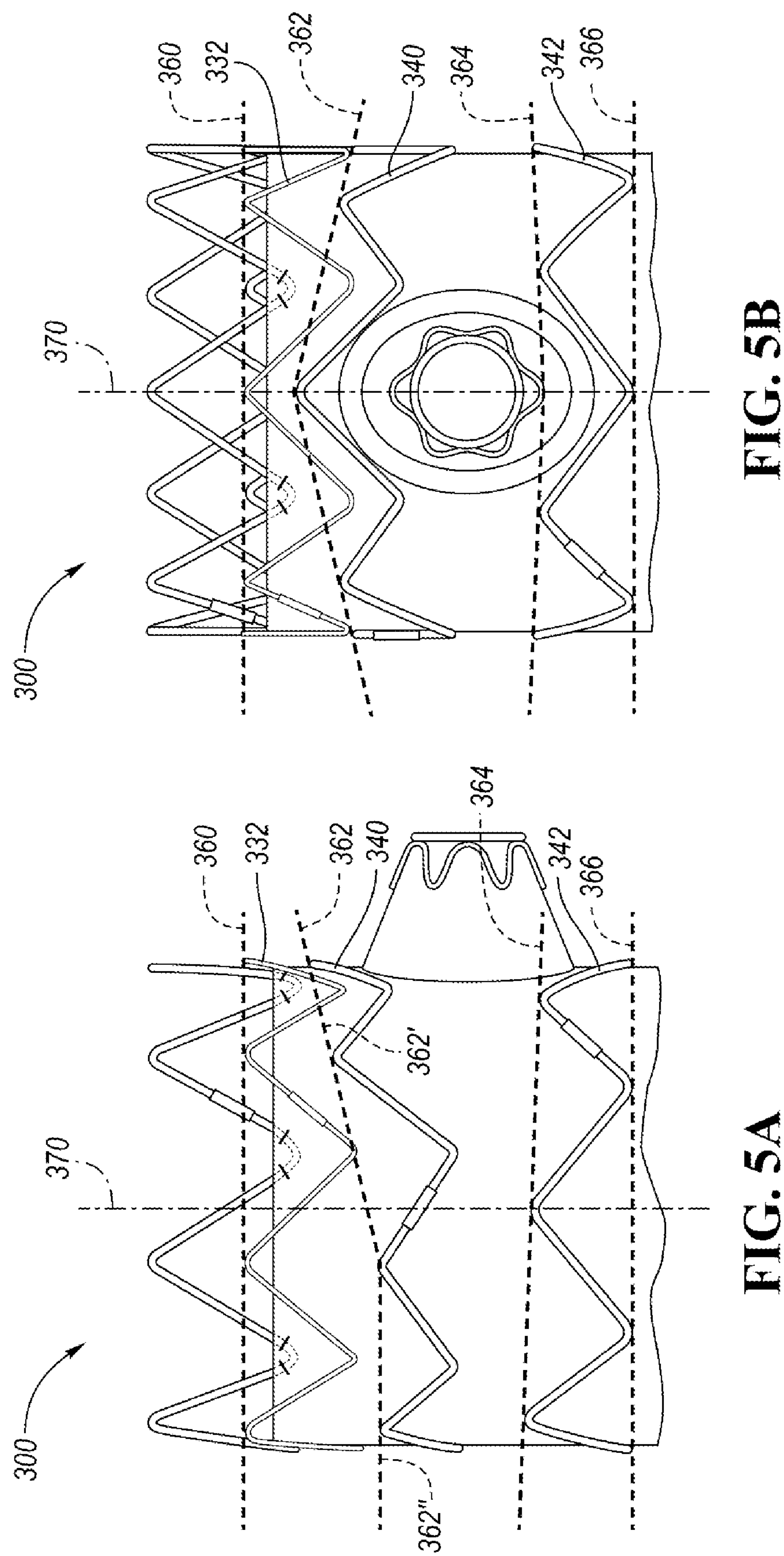
FIG. 5A is a similar view of FIG. 4A, with various axes shown that are described below.
FIG. 5B is a similar view of FIG. 4B, with various axes shown that are described below.

FIGS. 5A-5B are similar views of the stent graft 300 as FIGS. 4A-4B, now with focus on various axes. In particular, a first axis 360, a second axis 362, a third axis 364, and a fourth axis 366 are provided to illustrate various relationships that will be described.

The first axis 360 intersects the peaks 334, 336 of the support stent 332. In at least one embodiment, all of the peaks 334, 336 of the support stent 332 are circumferentially aligned about the stent graft 300 at a location proximally beyond the edge of the graft material 302. In other words, the axis 360 is perpendicular to a longitudinal axis 370. As described previously, a majority of the support stent 332 may be distal to the proximal edge of the graft material. In one embodiment, at least 50% of the axial length of the support stent 332 may be distal to the proximal edge of the graft material. In other embodiments, at least 60, 70, or 80% of the axial length of the support stent 332 may be distal to the proximal edge of the graft material. The peak of the support stent 332 may be completely proximal to the proximal edge of the graft material, such that there are two discrete contact points between the support stent 332 and the proximal edge of the graft material for each peak (e.g., one for each strut extending from the peak). Compared to a stent having a peak at the proximal edge of the graft material, which would have a single contact point, having the support stent 332 extend beyond the proximal edge of the graft material provides double the contact points and may improve the seal of the stent graft.

The second axis 362 intersects the peaks 344 of the first bracketing stent 340. The second axis 362 may include two sections 362', 362" having different slopes relative to the longitudinal axis 370. In at least one embodiment, the peaks 344 intersecting section 362' become closer to the proximal end 310 of the stent graft 300 as the peaks 344 become circumferentially closer to the coupling 320, with the peak 345 aligned with the coupling opening being the closest to the proximal end 310 of the stent graft 300. Section 362' may have a constant slope relative to the longitudinal axis 370, as shown in FIGS. 5A and 5B, or it may be non-constant but the intersected peaks 344 still continuously move closer to the proximal end as they become circumferentially closer to the coupling 320. Section 362" of second axis 362 may have a slope relative to longitudinal axis 370 that is less than section 362' (i.e., closer to perpendicular). In one embodiment, section 362" is perpendicular to longitudinal axis 370. The two sections may intersect at a peak 344 on either side of the coupling 320, such that two peaks of the support stent intersect with both sections 362' and 362". In one embodiment, all peaks 344 of the support stent intersect at least one of section 362' or 362" of the second axis 362. In the embodiment shown, section 362' intersects five peaks 344—the peak 345 aligned with the opening of the coupling 320 and two directly adjacent stent peaks on either circumferential side thereof. Section 362" intersects four peaks—the four peaks most circumferentially opposite the opening of the coupling 320. Accordingly, two peaks intersect both sections and are at a transition between the sloped section 362" and the perpendicular (in this embodiment) section 362". The dual sections of second axis 362 provide several benefits, such as providing the open area 346 of graft material 302 which provides additional flexibility for alignment of the coupling 320 within the treated vessel, as described above. This also allows for the first bracketing stent 340 to have proper spacing and support of the coupling 320 while maintaining proper alignment with the other stents at the side of the stent graft 300 opposite the coupling 320 (e.g., the left hand side of the view in FIG. 5A). While not shown with a separate axis, the valleys of first bracketing stent 340 that are adjacent to the peaks that intersect section 362" may also be aligned along a perpendicular axis parallel to section 362".

The third axis 364 intersects the peaks of the second bracketing stent 342. In at least one embodiment, the peaks of the second bracketing stent 342 become further away from the proximal end 310 of the stent graft 300 as the peaks becomes circumferentially closer to the coupling 320. In other words, the third axis 364 is oblique relative to longitudinal axis 370, and is not parallel to the first axis 360 or fourth axis 366. In the illustrated embodiment, the third axis 364 is linear, but in other embodiments the third axis 364 is non-linear similar to the second axis 362. The slope of the third axis 364 relative to the longitudinal axis 370 allows for proper spacing and support of the coupling 320 while maintaining proper alignment with the other stents at the side of the stent graft 300 opposite the coupling 320 (e.g., the left hand side of the view in FIG. 5A). Moreover, the third axis 364 does not intersect the opening 324, such that the peaks of the second bracketing stent 342 on the side of the main body where the coupling 320 is located (e.g., directly on either side of 320), are positioned distally of the opening 324. For example, referring to FIG. 5B, the third axis 364 never crosses over the opening 324 on the illustrated view of the stent graft 300 nor do those peaks axially overlap with the opening 324. The same may be true for the valleys of the first bracketing stent 340 on either side of the coupling 320—they may not intersect or overlap axially with the opening 324.

As can be seen in the illustrated embodiment in FIGS. 5A-5B, the second axis 362 allows for the "hi-lo" design described above. Also, the bracketing stents 340, 342 diverge about the coupling 320, but converge on the side of the stent graft 300 opposite the coupling 320. The spacing of the stents on the side of the stent graft 300 opposite the coupling 320 can be generally uniform, while the spacing of the stents on the side of the stent graft 300 with the coupling 320 can be non-uniform to make room for the coupling 320.

The fourth axis 366 intersects the valleys 350 of the second bracketing stent 342. In the illustrated embodiment, the fourth axis 366 is perpendicular to the longitudinal axis 370, and parallel to the first axis 360. However, in another embodiment, the fourth axis 366 is oblique relative to the longitudinal axis 370, and can be parallel to the third axis 364 or otherwise oblique. In the illustrated embodiment of FIGS. 5A-5B, the third axis 364 and fourth axis 366 create a wedge (e.g., in side-view shown in FIG. 5A), in that the fourth axis 366 is perpendicular to the longitudinal axis 370 while the third axis 364 is oblique to the longitudinal axis 370. This creates a "wedge" design, in which the valley-to-valley line is perpendicular to the longitudinal axis 370 but the peak-to-peak line gets higher (e.g., more proximal) toward the back of the stent graft 300 (e.g., the left-hand side of FIG. 5A). The amplitude or distance between the peaks and valleys increases in the direction toward the back of the stent graft 300. This can provide an open area 353 on either circumferential side of the coupling 320. The open area 353 can be an absence of stents, allowing the coupling 320 to move sideways (e.g., circumferentially relative to the axis 370) without interference from the bracketing stents 340, 342. This provides additional capabilities for mobility of the coupling 320.

While embodiments are described herein with respect to a branched stent graft, aspects of these embodiments may also be used in non-branched stent grafts (e.g., cylindrical or tubular stent grafts). For example, any of the proximal stent, support stent, first bracketing stent, and/or second bracketing stent may be incorporated into a non-branched stent graft in a similar manner as described herein.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A stent graft comprising:

a main body extending along a longitudinal axis and including proximal and distal ends; and an external coupling extending away from the main body and defining an opening having a center;

the main body includes a first bracketing stent extending along a proximal side of the external coupling, the first bracketing stent includes first and second peaks, the first peak circumferentially aligns with the center of the external coupling, and the first peak is proximal the second peak about the main body along the longitudinal axis, the first bracketing stent includes a first valley, the main body includes a second bracketing stent including second and third valleys, and the first and the second valleys longitudinally align on an opposite side of the main body from the external coupling.

2. The stent graft of claim 1, wherein the second peak is circumferentially offset from the external coupling.

3. The stent graft of claim 1, wherein the second peak is located between the external coupling and an opposite side of the main body from the external coupling.

4. The stent graft of claim 1, wherein the first bracketing stent includes a third peak distal the first peak and the second peak about the longitudinal axis of the main body.

5. The stent graft of claim 1, wherein the first bracketing stent includes a third peak and the second and the third peaks are each directly adjacent to the first peak and on opposite sides of the external coupling, the second and third peaks are aligned about the main body along the longitudinal axis and proximal to a remaining number of peaks of the first bracketing stent.

6. The stent graft of claim 1 further comprising a support stent including a support stent valley longitudinally aligning with the first and the second valleys and disposed proximal the first bracketing stent.

7. The stent graft of claim 1, wherein the first peak and the third valley longitudinally align at the external coupling.

8. A stent graft comprising:

a main body extending along a longitudinal axis and including proximal and distal ends; and an external coupling extending away from the main body;

the main body includes a second bracketing stent extending a distal side of the external coupling, the second bracketing stent includes a plurality of peaks aligned along a first axis and a plurality of valleys aligned along a second axis, the first axis is oblique to the longitudinal axis, and the second axis is perpendicular to the longitudinal axis, the main body includes a first bracketing stent extending a proximal side of the external coupling and including a first peak and a first valley, the plurality of valleys of the second bracketing stent includes second and third valleys, and the first and the second valleys longitudinally align on an opposite side of the main body from the external coupling.

9. The stent graft of claim 8 further comprising a support stent including a support stent valley longitudinally aligning with the first and the second valleys and disposed proximal the first bracketing stent.

10. The stent graft of claim 8, wherein distances between adjacent peaks and valleys of the plurality of peaks and valleys, respectively, along a circumferential region of the main body increase in a direction toward an opposite side of the main body from the external coupling to form an open region.

11. The stent graft of claim 10, wherein the open region is absent the second bracketing stent to facilitate circumferential movement of the external coupling relative to the longitudinal axis.

12. The stent graft of claim 8 further comprising an anchor stent including an anchor stent valley longitudinally aligning with the first and the second valleys and disposed proximal the first bracketing stent.

13. The stent graft of claim 8, wherein the first peak and the third valley longitudinally align at the external coupling.

14. A stent graft comprising:

a main body extending along a longitudinal axis and including proximal and distal ends; and an external coupling extending away from the main body, the main body includes an external coupling region including the external coupling and an opposite side region opposite the external coupling, the main body includes a first bracketing stent extending about a proximal side of the external coupling and a second bracketing stent extending a distal side of the external coupling, the first bracketing stent includes a first plurality of peaks aligned along a first axis having first and second sections, the second bracketing stent includes a second plurality of peaks aligned along a second axis having third and fourth sections, the first and the third sections are located in the external coupling region and diverge away from each other, and the second and the fourth sections are located in the opposite side region and converge toward each other, the first bracketing stent includes a first peak and a first valley, the second bracketing stent includes second and third valleys, and the first valley and the second valleys longitudinally align on an opposite side of the main body from the external coupling.

15. The stent graft of claim 14, wherein the first section has a constant slope relative to the longitudinal axis.

16. The stent graft of claim 14, wherein the third section has a third slope relative to the longitudinal axis, the fourth section has a fourth slope relative to the longitudinal axis, and the third and the fourth slopes are equal.

17. The stent graft of claim 14, wherein the first bracketing stent includes a first peak and a first valley, the second bracketing stent includes second and third valleys, and the first peak and the third valley longitudinally align at the external coupling.

18. The stent graft of claim 1 further comprising an anchor stent including an anchor stent valley longitudinally aligning with the first and the second valleys and disposed proximal the first bracketing stent.

19. The stent graft of claim 14 further comprising a support stent including a support stent valley longitudinally aligning with the first and the second valleys and disposed proximal the first bracketing stent.

20. The stent graft of claim 14 further comprising an anchor stent including an anchor stent valley longitudinally aligning with the first and the second valleys and disposed proximal the first bracketing stent.

* * * * *